United States Patent
Gers-Barlag et al.

(10) Patent No.: US 6,703,001 B1
(45) Date of Patent: Mar. 9, 2004

(54) COSMETIC AND DERMATOLOGICAL LIGHT-PROTECTIVE FORMULATIONS CONTAINING TRIAZINE DERIVATIVES ONE OR SEVERAL ESTERS OF BRANCHED-CHAIN CARBOXYLIC ACIDS AND BRANCHED-CHAIN ALCOHOLS

(75) Inventors: Heinrich Gers-Barlag, Kummerfeld (DE); Rainer Kröpke, Schenefeld (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/700,102

(22) PCT Filed: Apr. 22, 1999

(86) PCT No.: PCT/EP99/02708
§ 371 (c)(1),
(2), (4) Date: Nov. 9, 2000

(87) PCT Pub. No.: WO99/58102
PCT Pub. Date: Nov. 18, 1999

(30) Foreign Application Priority Data

May 9, 1998 (DE) .......................................... 198 20 827

(51) Int. Cl.⁷ .............................. A61K 7/42; A61K 7/40

(52) U.S. Cl. ......................................... 424/59; 514/242

(58) Field of Search ............................ 424/59; 514/242

(56) References Cited

U.S. PATENT DOCUMENTS

| 4,656,272 | A | * | 4/1987 | Martin et al. ................ 544/197 |
| 5,605,678 | A | * | 2/1997 | Ascione et al. ................ 424/59 |
| 5,759,525 | A | * | 6/1998 | Raspanti et al. ............... 424/59 |
| 5,843,410 | A | * | 12/1998 | Kim et al. ..................... 424/59 |
| 5,882,632 | A | * | 3/1999 | Allard et al. .................. 424/59 |
| 6,096,294 | A | * | 8/2000 | Hansenne et al. ............. 424/59 |
| 6,280,712 | B1 | * | 8/2001 | Ansmann et al. .............. 424/59 |

FOREIGN PATENT DOCUMENTS

JP 09241141 * 9/1997

* cited by examiner

*Primary Examiner*—Vickie Kim
(74) *Attorney, Agent, or Firm*—Norris McLaughlin & Marcus

(57) ABSTRACT

Active ingredient combinations comprising tris(2-ethylhexyl) 4,4',4"-(1,3,5-triazine-2,4,6-triyltriimino) trisbenzoate and one or more esters of branched-chain carboxylic acids and branched-chain alcohols.

5 Claims, No Drawings

COSMETIC AND DERMATOLOGICAL LIGHT-PROTECTIVE FORMULATIONS CONTAINING TRIAZINE DERIVATIVES ONE OR SEVERAL ESTERS OF BRANCHED-CHAIN CARBOXYLIC ACIDS AND BRANCHED-CHAIN ALCOHOLS

This application is a 371 of PCT/EP99/02708 filed on Apr. 22, 1999.

The present invention relates to cosmetic and dermatological light protection formulations, in particular skincare cosmetic and dermatological light protection preparations.

The harmful effect of the ultraviolet part of solar radiation on the skin is generally known. While rays with a wavelength of less than 290 nm (the so-called UVC region) are absorbed by the ozone layer in the earth's atmosphere, rays in the range between 290 nm and 320 nm, the so-called UVB range, cause erythema, simple sunburn or even burns of varying severity.

The maximum given for the erythema activity of sunlight is the narrower range around 308 nm.

Numerous compounds are known for protecting against UVB radiation; these are usually derivatives of 3-benzylidenecamphor, of 4-aminobenzoic acid, of cinnamic acid, of salicylic acid, of benzophenone and also of 2-phenylbenzimidazole.

It is also important to have available filters for the range between about 320 nm and about 400 nm, the so-called UVA region, since its rays can likewise cause damage. Thus, it has been found that UVA radiation leads to damage of the elastic and collagenous fibers of connective tissue, causing premature aging of the skin, and that it is to be regarded as a cause of numerous phototoxic and photoallergic reactions. The harmful effect of UVB radiation can be intensified by UVA radiation.

However, UV radiation can also lead to photochemical reactions, in which case the photochemical reaction products intervene in the skin's metabolism.

Such photochemical reaction products are predominantly free-radical compounds, e.g. hydroxyl radicals. Undefined free-radical photoproducts which form in the skin itself can also display uncontrolled secondary reactions because of their high reactivity. However, singlet oxygen, a non-radical excited state of the oxygen molecule, can also arise during UV radiation, as can short-lived epoxides and many other species. Singlet oxygen, for example, differs from the normal triplet oxygen (free-radical ground state) by virtue of its increased reactivity. However, excited reactive (free-radical) triplet states of the oxygen molecule also exist.

Furthermore, UV radiation is a type of ionizing radiation. There is therefore the risk that UV exposure may also produce ionic species which then, for their part, are capable of oxidative intervention in the biochemical processes.

An advantageous UVB filter is tris(2-ethylhexyl) 4,4',4"-(1,3,5-triazine-2,4,6-triyltriimino)trisbenzoate, also known as 2,4,6-tris-[anilino(p-carbo-2'-ethyl-1'-hexyloxy)]-1,3,5-triazine.

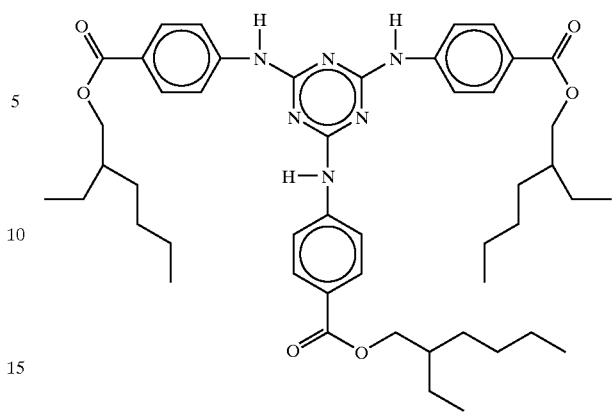

This UVB filter is sold by BASF Aktiengesellschaft under the trade name UVINUL7 T 150 and is notable for its good UV absorption properties.

The main disadvantage of this UVB filter is its poor solubility in lipids. Known solvents for this UVB filter can dissolve a maximum of about 15% by weight of this filter, corresponding to about 1–1.5% by weight of dissolved, and therefore active, UV filter substance.

It was nevertheless surprising, and could not have been foreseen by the person skilled in the art, that active ingredient combinations comprising tris(2-ethylhexyl) 4,4',4"-(1,3,5-triazine-2,4,6-triyltriimino)trisbenzoate and one or more esters of branched-chain carboxylic acids and branched-chain alcohols, or the use of one or more esters of branched-chain carboxylic acids and branched-chain alcohols as solvent, solubility promoter or solubilizer for tris(2-ethylhexyl) 4,4',4"-(1,3,5-triazine-2,4,6-triyltriimino) trisbenzoate, in particular for the use in light protection compositions, would overcome the disadvantages of the prior art.

The esters of branched-chain carboxylic acids and branched-chain alcohols according to the invention can advantageously be chosen from the group of substances of the general formula

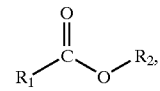

in which $R_1$ and $R_2$, independently of one another represent mono- or polybranched alkyl radicals having 3 to 30 carbon atoms.

$R_1$ is advantageously a mono- or polybranched alkyl radical having up to 10 carbon atoms.

In addition, $R_2$ is advantageously a mono- or polybranched alkyl radical having 5 to 20 carbon atoms.

It is particularly advantageous to use neopentanoic esters as carboxylic esters used according to the invention.

It is very particularly advantageous to use isodecyl neopentanoate as carboxylic ester used according to the invention. It has the chemical structure

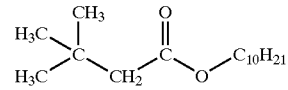

and is entered in the Chemical Abstracts under the registry number 60209-82-7. It is sold, for example, by Stearinerie Dubois under the name DUB VCI 10. As is known, it may be used in cosmetic and dermatological preparations as oil component.

It was nevertheless surprising that the addition of one or more esters of branched-chain carboxylic acids and branched-chain alcohols effects stabilization of solutions of tris(2-ethylhexyl) 4,4',4"-(1,3,5-triazine-2,4,6-triyltriimino) trisbenzoate, since the latter substance not only has poor solubility, but also readily crystallizes out again from its solution. The invention therefore also provides a method of stabilizing solutions of tris(2-ethylhexyl) 4,4',4"-(1,3,5-triazine-2,4,6-triyltriimino)trisbenzoate, which comprises adding an effective content of one or more esters of branched-chain carboxylic acids and branched-chain alcohols to such solutions.

The total amount of tris(2-ethylhexyl) 4,4',4"-(1,3,5-triazine-2,4,6-triyltriimino)trisbenzoate in the finished cosmetic or dermatological preparations is advantageously chosen from the range 0.1–10.0% by weight, preferably 0.5–6.0% by weight, based on the total weight of the preparations.

The total amount of one or more esters of branched-chain carboxylic acids and branched-chain alcohols in the finished cosmetic or dermatological preparations is advantageously chosen from the range 0.1–25.0% by weight, preferably 0.5–15.0% by weight, based on the total weight of the preparations.

It is advantageous to choose weight ratios of tris(2-ethylhexyl) 4,4',4"-(1,3,5-triazine-2,4,6-triyltriimino) trisbenzoate and one or more esters of branched-chain carboxylic acids and branched-chain alcohols from the range 1:10 to 10:1, preferably 1:4 to 4:1.

Cosmetic and dermatological preparations according to the invention also advantageously comprise inorganic pigments based on metal oxides and/or other metal compounds which are sparingly soluble or insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides. Pigments based on $TiO_2$ are particularly preferred.

For the purposes of the present invention, it is particularly advantageous, although not imperative, if the inorganic pigments are present in hydrophobic form, i.e. they have been surface-treated to repel water. This surface treatment can consist in providing the pigments with a thin hydrophobic layer by processes known per se.

One such process consists, for example, in producing the hydrophobic surface layer by the reaction according to:

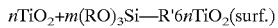

$n TiO_2 + m(RO)_3 Si—R' 6n TiO_2 (surf.)$ where n and m are arbitrary stoichiometric parameters and R and R' are the desired organic radicals. Hydrophobicized pigments prepared analogously to DE-A 33 14 742, for example, are advantageous.

Advantageous $TiO_2$ pigments are available, for example, under the trade names MT 100 T from TAYCA, also M 160 from Kemira and T 805 from Degussa.

The cosmetic and/or dermatological light protection formulations according to the invention can have the conventional compositions and can be used for cosmetic and/or dermatological light protection, and also for the treatment, care and cleansing of the skin and/or hair and as make-up products in decorative cosmetics.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously, these can additionally comprise at least one further UVA filter and/or at least one further UVB filter and/or at least one inorganic pigment, preferably an inorganic micropigment.

The cosmetic and dermatological preparations according to the invention can comprise cosmetic auxiliaries such as those customarily used in such preparations, e.g. preservatives, bactericides, perfumes, antifoams, dyes, pigments which have a coloring effect, thickeners, moisturizers and/or humectants, fats, oils, waxes, or other customary constituents of a cosmetic or dermatological formulation, such as alcohols, polyols, polymers, foam stabilizers, electrolytes, organic solvents or silicone derivatives.

An additional content of antioxidants is generally preferred. According to the invention, favorable antioxidants which can be used are all antioxidants suitable or customary for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine-sulfoximines, homocysteine-sulfoximine, buthionine-sulfones, penta-, hexa-, heptathionine-sulfoximines) in very low tolerated doses (e.g. pmol to µmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active ingredients which are suitable according to the invention.

The amount of the abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are used as the antioxidant or antioxidants, their respective concentrations are advantageously chosen from the range 0.001–10% by weight, based on the total weight of the formulation.

If vitamin A or vitamin A derivatives or carotenes or derivatives thereof are used as the antioxidant or antioxidants, their respective concentrations are advantageously chosen from the range 0.001–10% by weight, based on the total weight of the formulation.

The lipid phase can advantageously be chosen from the following group of substances:

mineral oils, mineral waxes oils, such as triglycerides of capric or of caprylic acid, but preferably castor oil;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alkyl benzoates;

silicone oils such as dimethylpolysiloxanes, diethylpolysiloxanes, diphenylpolysiloxanes and mixtures thereof.

For the purposes of the present invention, the oil phase of the emulsions, oleogels and hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oil phase can also advantageously be chosen from the group of branched and unbranched hydrocarbons and hydrocarbon waxes, of silicone oils, of dialkyl ethers, from the group of saturated or unsaturated, branched or unbranched alcohols, and also fatty acid triglycerides, namely the triglycerol esters of saturated and/or unsaturated, branched and/or unbranched alkanecarboxylic acids having a chain length of from 8 to 24, in particular 12–18, carbon atoms. The fatty acid triglycerides can advantageously be chosen, for example, from the group of synthetic, semi-synthetic and natural oils, e.g. olive oil, sunflower oil, soybean oil, groundnut oil, rapeseed oil, almond oil, palm oil, coconut oil, palm kernel oil and the like.

For the purposes of the present invention, any mixtures of such oil and wax components can also advantageously be used. When required, it can also be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12}$–$C_{15}$-alkyl benzoate, caprylic/capric triglyceride and dicaprylyl ether.

Mixtures of $C_{12}$–$C_{15}$-alkyl benzoate and 2-ethylhexyl isostearate, mixtures of $C_{12}$–$C_{15}$-alkyl benzoate and isotridecyl isononanoate and mixtures of $C_{12}$–$C_{15}$-alkyl benzoate, 2-ethylhexyl isostearate and isotridecyl isononanoate are particularly advantageous.

For the purposes of the present invention, of the hydrocarbons, paraffin oil, squalane and squalene can advantageously be used.

The oil phase can advantageously also contain cyclic or linear silicone oils or can consist entirely of such oils, although it is preferable to use an additional content of other oil phase components in addition to the silicone oil or silicone oils.

Cyclomethicone(octamethylcyclotetrasiloxane) is advantageously used as silicone oil to be used according to the invention. However, other silicone oils can also be used advantageously for the purposes of the present invention, for example hexamethylcyclotrisiloxane, polydimethylsiloxane, poly(methylphenylsiloxane).

Mixtures of cyclomethicone and isotridecyl isononanoate and mixtures of cyclomethicone and 2-ethylhexyl isostearate are particularly advantageous.

The aqueous phase of the preparations according to the invention may advantageously comprise alcohols, diols or polyols of low carbon number, and also ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and in particular one or more thickeners which can advantageously be chosen from the group consisting of silicon dioxide, aluminum silicates, polysaccharides and derivatives thereof, e.g. hyaluronic acid, xanthan gum, hydroxypropylmethylcellulose, and particularly advantageously from the group of polyacrylates, preferably a polyacrylate from the group of the so-called Carbopols, for example Carbopol grades 980, 981, 1382, 2984, 5984, in each case individually or in combination.

The cosmetic or dermatological light protection preparations advantageously comprise inorganic pigments, in particular micropigments, e.g. in amounts of from 0.1% by weight to 30% by weight, preferably in amounts of from 0.5% by weight to 10% by weight, but in particular from 1% by weight to 6% by weight, based on the total weight of the preparations.

It is advantageous according to the invention to use, apart from the combinations according to the invention, oil-soluble UVA filters and/or UVB filters in the lipid phase and/or water-soluble UVA filters and/or UVB filters in the aqueous phase.

The light protection formulations according to the invention can advantageously comprise further substances which absorb UV radiation in the UVB region, the total amount of filter substances being e.g. from 0.1% by weight to 30% by weight, preferably from 0.5 to 10% by weight, in particular from 1 to 6% by weight, based on the total weight of the preparations, in order to provide cosmetic preparations which protect the skin from the entire range of ultraviolet radiation. They can also be used as sunscreens.

The further UVB filters can be oil-soluble or water-soluble. Examples of advantageous oil-soluble UVB filter substances are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzmalonic acid, preferably di(2-ethylhexyl) 4-methoxybenzmalonate.

Examples of advantageous water-soluble UVB filter substances are:

salts of 2-phenylbenzimidazole-5-sulfonic acid, such as its sodium, potassium or its triethanolammonium salt, and also the sulfonic acid itself;

sulfonic acid derivatives of benzophenones, preferably 2-hydroxy-4-methoxybenzophenone-5-sulfonic acid and salts thereof;

sulfonic acid derivatives of 3-benzylidenecamphor, such as e.g. 4-(2-oxo-3-bornylidenemethyl)benzenesulfonic acid, 2-methyl-5-(2-oxo-3-bornylidene-methyl) sulfonic acid and salts thereof.

The list of said further UVB filters which can be used in combination with the active ingredient combinations according to the invention is of course not intended to be limiting.

It can also be advantageous to combine the combinations according to the invention with further UVA filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. These combinations and preparations which contain these combinations are also provided by the invention. The amounts which may be used are as for the UVB combination.

It is further advantageous to combine the active ingredient combinations according to the invention with further UVA and/or UVB filters.

It is also particularly advantageous to combine the active ingredient combinations according to the invention with salicylic acid derivatives, some of which, as is known, can also absorb UV radiation. Customary UV filters include

(4-isopropylbenzyl salicylate),

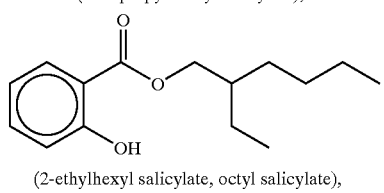

(2-ethylhexyl salicylate, octyl salicylate),

-continued

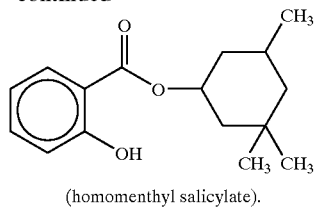

(homomenthyl salicylate).

The invention further provides a process for the preparation of the cosmetic and/or dermatological light protection preparations according to the invention, which comprises suspending and, if desired, homogenizing tris(2-ethylhexyl) 4,4',4"-(1,3,5-triazine-2,4,6-triyltriimino)trisbenzoate in one or more esters of branched-chain carboxylic acids and branched-chain alcohols or an oil phase containing one or more esters of branched-chain carboxylic acids and branched-chain alcohols with uniform stirring and if necessary with warming, where appropriate combining the mixture with further lipid components and optionally with one or more emulsifiers, then mixing the oil phase with the aqueous phase into which a thickener has optionally been incorporated and which is preferably at the same temperature as the oil phase, if desired homogenizing the mixture, and allowing it to cool to room temperature. After the mixture has cooled to room temperature, homogenization may be repeated, particularly if volatile constituents are still to be incorporated.

The examples below serve to illustrate the present invention without limiting it. Unless indicated otherwise, all amounts, proportions and percentages are based on the weight and the total amount or on the total weight of the preparations.

|  | % by weight |
|---|---|
| Example 1 |  |
| O/W emulsion |  |
| Stearic acid | 3.50 |
| Glycerol | 3.00 |
| Cetylstearyl alcohol | 0.50 |
| Dicaprylyl ether | 8.00 |
| Uvinul ® T150 | 5.00 |
| Isodecyl neopentanoate | 12.00 |
| Sodium hydroxide (45% strength) | 0.33 |
| Carbomer | 0.20 |
| Preservative | q.s. |
| Perfume | q.s. |
| Water, demin. | ad 100.00 |
| Example 2 |  |
| W/O emulsion |  |
| Arlacel ® 989 | 5.50 |
| Butylene glycol | 5.00 |
| Isodecyl neopentanoate | 12.00 |
| Uvinul ® T150 | 5.00 |
| Cetylstearyl isononanoate | 6.00 |
| Carbomer | 0.20 |
| Preservative | q.s. |
| Perfume | q.s. |
| Water, demin. | ad 100.00 |
| Example 3 |  |
| Hydrodispersion gel |  |
| Carbomer | 0.50 |
| Butylene glycol | 5.00 |
| Isodecyl neopentanoate | 10.00 |
| Sodium hydroxide (45% strength) | 0.35 |

-continued

|  | % by weight |
|---|---|
| Uvinul ® T150 | 5.00 |
| Hydroxypropylcellulose | 0.60 |
| Preservative | q.s. |
| Perfume | q.s. |
| Water, demin. | ad 100.00 |

What is claimed is:

1. A method of stabilizing a solution comprising tris(2-ethylhexyl) 4,4',4"-(1,3,5-triazine-2,4,6-tryltriimino)trisbenzoate against crystallization of said tris(2-ethylhexyl) 4,4',4"-(1,3,5-triazine-2,4,6-triyltriimino)trisbenzoate from said solution, said method comprising a) incorporating in said solution isodecyl neopentanoate in an amount sufficient to prevent said crystallization and b) achieving a stabilization of said solution against said crystallization.

2. The method according to claim 1, wherein said solution comprises 0.1 to 10.0% by weight of tris(2-ethylhexyl) 4,4',4"-(1,3,5-triazine-2,4,6-triyltriimino)trisbenzoate based on the total weight of the solution.

3. The method according to claim 1, wherein said solution comprises 0.5 to 6.0% by weight of tris(2-ethylhexyl) 4,4', 4"-(1,3,5-triazine-2,4,6-triyltriimino)trisbenzoate based on the total weight of the solution.

4. The method according to claim 1, wherein said solution comprises a total of 0.1 to 25.0% by weight of said isodecyl neopentanoate based on the total weight of the solution.

5. The method according to claim 1, wherein said solution comprises a total of 0.5 to 15.0% by weight of said isodecyl neopentanoate based on the total weight of the solution.

* * * * *

UNITED STATES PATENT AND TRADEMARK OFFICE
CERTIFICATE OF CORRECTION

PATENT NO.    : 6,703,001 B1
DATED         : March 9, 2004
INVENTOR(S)   : Gers-Barlag et al.

It is certified that error appears in the above-identified patent and that said Letters Patent is hereby corrected as shown below:

<u>Title page,</u>
Item [54], Title, "ONE OR SEVERAL ESTERS OF" should read -- AND ONE OR SEVERAL ESTERS OF --

Signed and Sealed this

Twelfth Day of October, 2004

JON W. DUDAS
*Director of the United States Patent and Trademark Office*